(12) United States Patent
Grashow et al.

(10) Patent No.: US 11,607,516 B2
(45) Date of Patent: Mar. 21, 2023

(54) PROVIDING SLEEP THERAPY WITH A PRESSURE THERAPY SYSTEM

(71) Applicant: KONINKLIJKE PHILIPS N.V., Eindhoven (NL)

(72) Inventors: Jonathan Sayer Grashow, Pittsburgh, PA (US); Eugene Nelson Scarberry, Trafford, PA (US); Gregory Delano Matthews, Pittsburgh, PA (US); Michael Thomas Kane, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 828 days.

(21) Appl. No.: 16/546,978

(22) Filed: Aug. 21, 2019

(65) Prior Publication Data

US 2020/0061325 A1 Feb. 27, 2020

Related U.S. Application Data

(60) Provisional application No. 62/722,306, filed on Aug. 24, 2018.

(51) Int. Cl.
*A61M 16/06* (2006.01)
*A61M 16/00* (2006.01)
(Continued)

(52) U.S. Cl.
CPC ....... *A61M 16/0666* (2013.01); *A61B 5/0826* (2013.01); *A61M 16/0003* (2014.02);
(Continued)

(58) Field of Classification Search
CPC ......... A61B 5/087; A61B 5/316; A61B 5/369; A61B 5/375; A61B 5/38; A61B 5/389;
(Continued)

(56) References Cited

U.S. PATENT DOCUMENTS 6,349,724 B1 * 2/2002 Burton .................. F04D 29/052
128/204.22
6,397,845 B1 6/2002 Burton
(Continued)

OTHER PUBLICATIONS

Sound Oasis Sound Therapy System, 2018 Amazon.com, Link: https://www.amazon.com/Sound-Oasis-Therapy-System/dp/B001H36B5W.
(Continued)

*Primary Examiner* — Annette Dixon
(74) *Attorney, Agent, or Firm* — Michael W. Haas (57) ABSTRACT

The present disclosure pertains to a system configured to enhance deep sleep in a subject during positive airway pressure therapy. A pressure generator is configured to generate a pressurized flow of breathable gas for delivery to an airway of the subject. Sensors are configured to generate output signals conveying information related to breathing of the subject. One or more hardware processors are configured to cause the pressure generator to generate the pressurized flow of breathable gas in accordance with a positive airway pressure therapy regime based on the information in the output signals; determine sleep stages of the subject based on the information in the output signals; and responsive to the sleep stages indicating the subject is in deep sleep, cause the pressure generator to adjust the pressurized flow of breathable gas to deliver a stimulus to the subject, the stimulus configured to enhance deep sleep in the subject.

15 Claims, 4 Drawing Sheets

(51) Int. Cl.
*A61M 21/00* (2006.01)
*A61B 5/08* (2006.01)
*A61M 16/04* (2006.01)
*A61B 5/00* (2006.01)

(52) U.S. Cl.
CPC ........ *A61M 16/0683* (2013.01); *A61M 21/00* (2013.01); *A61B 5/4812* (2013.01); *A61B 5/4815* (2013.01); *A61B 5/4818* (2013.01); *A61M 16/0488* (2013.01); *A61M 2210/0625* (2013.01)

(58) Field of Classification Search
CPC ..... A61B 5/398; A61B 5/4812; A61B 5/4815; A61B 5/4818; A61B 5/4836; A61B 5/4857; A61B 5/6803; A61B 5/6814; A61B 5/6831; A61B 5/721; A61B 5/7221; A61B 5/7235; A61B 5/7242; A61B 5/7275; A61F 5/566; A61K 2300/00; A61K 31/00; A61K 31/4412; A61K 31/4425; A61K 33/00; A61K 45/06; A61M 16/0057; A61M 16/0066; A61M 16/0069; A61M 16/107; A61M 2016/0036; A61M 2021/0027; A61M 21/00; A61M 21/02; A61M 2205/505; A61M 2205/52; A61M 2230/005; A61M 2230/10; A61M 2230/18; A61M 2230/60; A61M 2230/63; A61M 31/00; A61P 11/00; A61P 11/16; F04D 25/166; F04D 29/052; F04D 29/286
See application file for complete search history.

(56) References Cited

U.S. PATENT DOCUMENTS

| | | | |
|---|---|---|---|
| 2005/0217674 A1 | 10/2005 | Burton et al. | |
| 2006/0149216 A1* | 7/2006 | Sherman | A61K 33/00 604/503 |
| 2008/0127978 A1 | 6/2008 | Depetrilllo et al. | |
| 2010/0240982 A1* | 9/2010 | Westbrook | A61B 5/4818 600/538 |
| 2014/0238412 A1* | 8/2014 | Fan | A61M 16/0057 514/346 |
| 2017/0304587 A1* | 10/2017 | Santostasi | A61B 5/7242 |
| 2017/0312476 A1 | 11/2017 | Woo | |

OTHER PUBLICATIONS

Bellesi M. et al., "Enhancement of Sleep Slow Waves: Underlying Mechanisms and Practical Consequences", Frontiers in Systems Neuroscience, Oct. 2014 | vol. 8 | Article 208, pp. 1-17.

Bosak K. et al., "Does listening to delta wave sleep music while sleeping really help you get deep NREM sleep or the so called slow wave sleep?", Answers from Quora by Katarzyna Bosak, Research Specialist at Nightly updated Apr. 11, 2018.

* cited by examiner

PROVIDING SLEEP THERAPY WITH A PRESSURE THERAPY SYSTEM

CROSS-REFERENCE TO RELATED APPLICATIONS

This patent application claims the priority benefit under 35 U.S.C. § 119(e) of U.S. Provisional Application No. 62/722,306, filed on Aug. 24, 2018, the contents of which are herein incorporated by reference.

BACKGROUND OF THE INVENTION

1. Field of the Invention

The present disclosure pertains to a system and method for enhancing deep sleep in a subject during positive airway pressure therapy.

2. Description of the Related Art

Deep sleep enhancement devices are known. These devices typically measure brainwave activity via electroencephalogram (EEG) electrodes and play audible tones via earphone speakers, which enhances slow wave activity in the brain during deep sleep. These systems do not typically monitor respiration to detect deep sleep or deliver sensory stimulation to enhance deep sleep as part of pressure support respiratory therapy.

SUMMARY OF THE INVENTION

Accordingly, one or more aspects of the present disclosure relate to a system configured to enhance deep sleep in a subject during positive airway pressure therapy. The system comprises a pressure generator, one or more sensors, one or more processors, and/or other components. The pressure generator is configured to generate a pressurized flow of breathable gas for delivery to an airway of the subject. The one or more sensors are configured to generate output signals conveying information related to breathing of the subject. The one or more hardware processors are operatively coupled to the pressure generator and the one or more sensors. The one or more hardware processors are configured by machine-readable instructions to cause the pressure generator to generate the pressurized flow of breathable gas in accordance with a positive airway pressure therapy regime based on the information in the output signals. The one or more hardware processors are configured to determine sleep stages of the subject based on the information in the output signals. Responsive to the sleep stages indicating the subject is in deep sleep, the one or more hardware processors are configured to cause the pressure generator to adjust the pressurized flow of breathable gas to deliver a stimulus to the subject. The stimulus is configured to enhance deep sleep in the subject.

Another aspect of the present disclosure relates to a method for enhancing deep sleep in a subject during positive airway pressure therapy with an enhancement system. The system comprises a pressure generator, one or more sensors, and one or more hardware processors configured by machine-readable instructions. The method comprises generating, with the pressure generator, a pressurized flow of breathable gas for delivery to an airway of the subject. The method comprises generating, with the one or more sensors, output signals conveying information related to breathing of the subject. The method comprises causing, with the one or more hardware processors, the pressure generator to generate the pressurized flow of breathable gas in accordance with a positive airway pressure therapy regime based on the information in the output signals. The method comprises determining, with the one or more hardware processors, sleep stages of the subject based on the information in the output signals. The method comprises, responsive to the sleep stages indicating the subject is in deep sleep, causing, with the one or more hardware processors, the pressure generator to adjust the pressurized flow of breathable gas to deliver a stimulus to the subject. The stimulus is configured to enhance deep sleep in the subject.

Still another aspect of the present disclosure relates to a system for enhancing deep sleep in a subject during positive airway pressure therapy. The system comprises means for generating a pressurized flow of breathable gas for delivery to an airway of the subject. The system comprises means for generating output signals conveying information related to breathing of the subject. The system comprises means for causing the means for generating the pressurized flow of breathable gas to generate the pressurized flow of breathable gas in accordance with a positive airway pressure therapy regime based on the information in the output signals. The system comprises means for determining sleep stages of the subject based on the information in the output signals. The system comprises means for, responsive to the sleep stages indicating the subject is in deep sleep, causing the means for generating the pressurized flow of breathable gas to adjust the pressurized flow of breathable gas to deliver a stimulus to the subject. The stimulus is configured to enhance deep sleep in the subject.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
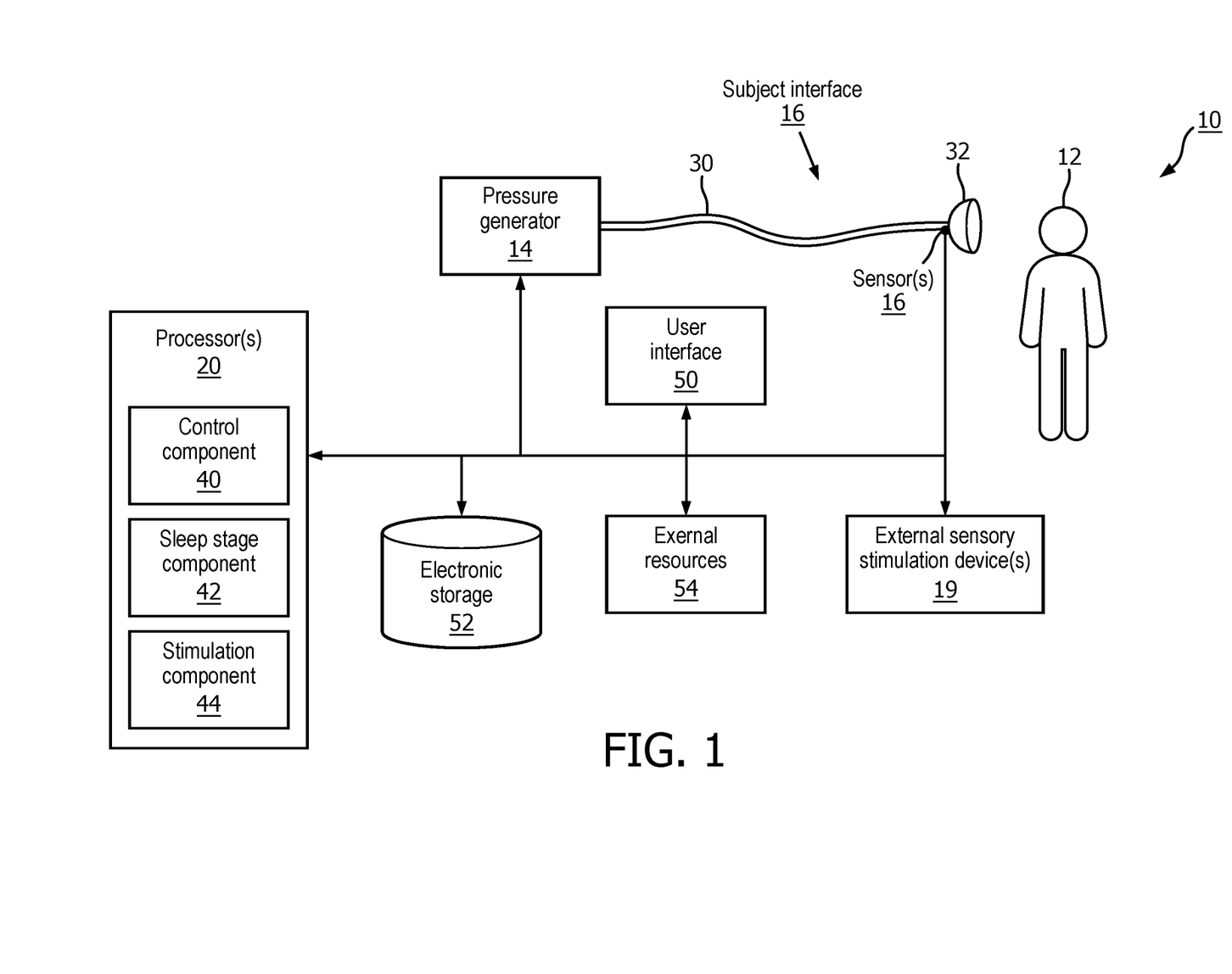
FIG. 1 is a schematic illustration of a system configured to enhance deep sleep in a subject during positive airway pressure therapy.

FIG. 1 is a schematic illustration of a system 10 configured to enhance deep sleep in a subject 12 during positive airway pressure therapy. The positive airway pressure therapy is delivered to subject 12 during a sleep session and/or at other times. A sleep session may be and/or include a night of sleep, a nap, and/or other sleep sessions. System 10 is configured to provide positive airway pressure therapy during the sleep session in the form of a pressurized flow of breathable gas that is delivered to the airway of subject 12. System 10 is configured to treat obstructive sleep apnea, chronic obstructive pulmonary disorder (COPD), dyspnea, Cheyne-Stokes respiration, apnea, and/or other disordered breathing. In combination with treating sleep disordered breathing, system 10 is configured to enhance deep sleep in subject 12 (e.g., which may be part of the sleep disordered breathing treatment). Advantageously, system 10 is configured to provide respiratory and sleep therapy without numerous and possibly overlapping components (e.g., wiring, sensors, electrodes, hoses, stimulation devices, etc.) that may result from simply using a traditional sleep therapy device at the same time as a traditional pressure support device.

Deep sleep may be and/or include slow wave sleep, delta sleep, N3 sleep, and/or other sleep. Enhancing deep sleep may include facilitating transitions from lighter sleep stages to deeper sleep stages, maintaining subject 12 in deeper sleep stages, and/or other enhancement by monitoring the respiratory activity of subject 12 (which may also be indicative of brain activity), and providing stimulation to subject 12 to enhance deep sleep. The stimulation is configured to enhance deep sleep in subject 12. In system 10, the stimulation may be provided by adjusting the pressurized flow of breathable gas delivered to subject 12, and/or by providing other sensory stimulation to subject 12 (e.g., as described below).

Normal sleep is characterized by sleep stages which occur in a cyclic manner (e.g., sleep cycles) and have a different contribution to the restorative value of sleep. The sleep stages of subject 12 may be associated with rapid eye movement (REM) sleep, non-rapid eye movement (NREM) sleep, and/or other sleep. The sleep stages of subject 12 may be one or more of NREM stage N1, stage N2, or stage N3 sleep, REM sleep, wakefulness, and/or other sleep stages. In some embodiments, NREM stage N3 sleep may be slow wave (e.g., deep) sleep. Stage N1 and N2 are the stages of light sleep, normally characterized by theta (4-8 Hz) oscillatory brain activity, sleep spindles, and K-complexes. Stage N3 is the stage of deep sleep, characterized by slow waves and delta activity (0.5-4 Hz). REM sleep typically occurs after around 90 minutes of sleep onset and is characterized by increased eye movement, hearth rate, and/or respiration. Wakefulness is a period just before or just after sleep when subject 12 is still alert.

In some embodiments, system 10 comprises one or more of a pressure generator 14, a subject interface 16, one or more sensors 18, one or more external sensory stimulation devices 19, one or more processors 20, a user interface 50, electronic storage 52, external resources 54, and/or other components.

Pressure generator 14 is configured to generate a pressurized flow of breathable gas for delivery to the airway of subject 12. Pressure generator 14 may control one or more parameters of the flow of gas (e.g., flow rate, pressure, volume, temperature, duration, a timing, gas composition, etc.) for therapeutic purposes, and/or for other purposes. By way of a non-limiting example, pressure generator 14 may be configured to generate the therapeutic pressurized flow of breathable gas, and the adjustment to the pressurized flow of breathable gas to deliver a stimulus to the subject. The stimulus may have associated amplitude, period, timing, and/or other parameters configured to enhance deep sleep in subject 12.

Pressure generator 14 receives a flow of gas from a gas source, such as the ambient atmosphere, and elevates and/or reduces the pressure of that gas for delivery to the airway of subject 12. Pressure generator 14 is any device, such as, for example, a pump, blower, piston, or bellows, that is capable of elevating and/or reducing the pressure of the received gas for delivery to subject 12. Pressure generator 14 may comprise one or more valves for controlling the pressure and/or flow of gas, for example. The present disclosure also contemplates controlling the operating speed of the blower, either alone or in combination with such valves, to control the pressure and/or flow of gas provided to subject 12.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit, that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full-face mask, a total facemask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensor 18 is configured to generate output signals conveying information related to breathing of subject 12 and/or other information. Sensor 18 is configured such that generating output signals conveying information related to breathing of subject 12 comprises generating output signals conveying information related to one or more gas parameters of the pressurized flow of breathable gas. Sensor 18 is configured such that generating output signals conveying information related to breathing of subject 12 comprises generating output signals conveying information related to one or more breathing parameters related to the respiration of subject 12. The one or more gas parameters and/or the one or more breathing parameters may comprise one or more of a flow rate, a volume, a pressure, a composition (e.g., concentration(s) of one or more constituents), temperature, humidity, acceleration, velocity, acoustics, changes in a parameter indicative of respiratory effort by subject 12, a timing, a duration, a frequency, a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other parameters. Sensor 18 may comprise one or more sensors that measure such parameters directly (e.g., through fluid communication with the flow of gas in subject interface 16). Sensor 18 may comprise one or more sensors that generate output signals related to one or more parameters of the flow of gas indirectly. For example, one or more sensors 18 may generate an output based on an operating parameter of pressure generator 14 (e.g., a valve driver or motor current, voltage, rotational velocity, and/or other operating parameters).

In some embodiments, sensor 18 may comprise one or more sensors that measure brain activity of subject 12 directly. For example, sensor 18 may include EEG electrodes configured to detect electrical activity along the scalp of subject 12 resulting from current flows within the brain of subject 12. Sensor 18 may comprise one or more sensors that generate output signals conveying information related to activity of subject 12 indirectly. For example, one or more sensor 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), and/or other characteristics of subject 12. In some embodiments, the one or more sensors comprise one or more of the EEG electrode, an electrooculogram (EOG) electrode, an actigraphy sensor, an electrocardiogram (EKG) electrode, a pressure (movement) sensor, a vital signs camera, a photoplethysmogram (PPG) sensor, a functional near infra-red sensor (fNIR), a temperature sensor, and/or other sensors.

Although sensor 18 is illustrated at a single location within (or in communication with) conduit 30 between interface appliance 32 and pressure generator 14, this is not intended to be limiting. Sensor 18 may include sensors disposed in a plurality of locations, such as for example, within pressure generator 14, within (or in communication with) interface appliance 32, in communication with subject 12, and/or in other locations.

System 10 may include external sensory stimulation device 19 in some embodiments, but not others. In embodiments that include external sensory stimulation device 19, external sensory stimulation device 19 is configured to provide sensory stimulation to subject 12. External sensory stimulation device 19 is configured to provide auditory, visual, somatosensory, electric, magnetic, and/or other sensory stimulation to subject 12 prior to a sleep session, during a sleep session, and/or at other times. In some embodiments, as described above, a sleep session may comprise any period of time when subject 12 is sleeping and/or attempting to sleep. Sleep sessions may include nights of sleep, naps, and/or other sleeps sessions. For example, sensory external sensory stimulation device 19 may be configured to provide stimuli to subject 12 during a sleep session to facilitate a transition to a deeper stage of sleep, a lighter stage of sleep, maintain sleep in a specific stage, enhance the restorative effects of sleep, and/or for other purposes. In some embodiments, external sensory stimulation device 19 may be configured such that facilitating a transition between deeper sleep stages and lighter sleep stages includes decreasing sleep slow waves in subject 12, and facilitating a transition between lighter sleep stages and deeper sleep stages includes increasing sleep slow waves.

External sensory stimulation device 19 is configured to facilitate transitions between sleep stages, maintain sleep in a specific stage, and/or enhance the restorative effects of sleep through non-invasive brain stimulation and/or other methods. External sensory stimulation device 19 may be configured to facilitate transitions between sleep stages, maintain sleep in a specific stage, and/or enhance the restorative effects of sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. For example, acoustic tones may be provided to subject 12 to enhance the restorative effects of sleep in subject 12.

The acoustic tones may include one or more series of 50-millisecond long (for example) tones separated from each other by a fixed one second long (for example) intertone interval. The volume of individual tones may be modulated by sleep depth such that loud (soft) tones are played during deeper (shallower) sleep. This example is not intended to be limiting. Examples of external sensory stimulation device 19 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, external sensory stimulation device 19 is configured to adjust the intensity, timing, and/or other parameters of the stimulation provided to subject 12.

Processor 20 is configured to provide information-processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., pressure generator 14, sensor 18, user interface 50, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a control component 40, a sleep stage component 42, a stimulation component 44, and/or other components. Processor 20 may be configured to execute components 40, 42, and/or 44 by software; hardware; firmware; some combination of software, hardware, and/or firmware; and/or other mechanisms for configuring processing capabilities on processor 20.

It should be appreciated that although components 40, 42, and 44 are illustrated in FIG. 1 as being co-located within a single processing unit, in embodiments in which processor 20 comprises multiple processing units, one or more of components 40, 42, and/or 44 may be located remotely from the other components. The description of the functionality provided by the different components 40, 42, and/or 44 described below is for illustrative purposes, and is not intended to be limiting, as any of components 40, 42, and/or 44 may provide more or less functionality than is described. For example, one or more of components 40, 42, and/or 44 may be eliminated, and some or all of its functionality may be provided by other components 40, 42, and/or 44. As another example, processor 20 may be configured to execute one or more additional components that may perform some or all of the functionality attributed below to one of components 40, 42, and/or 44.

Control component 40 is configured to cause pressure generator 14 to generate the pressurized flow of breathable gas in accordance with a positive airway pressure therapy regime. Control component 40 is configured to cause pressure generator 14 to generate the pressurized flow of breathable gas based on the information in the output signals, information entered by a user (e.g., subject 12, a caregiver, a family member, a friend, etc.) to user interface 50, and/or other information. In some embodiments, the positive airway pressure therapy regime is a positive airway positive airway pressure therapy regime. In positive airway positive airway pressure therapy the pressurized flow of gas generated by pressure generator 14 is controlled to replace and/or compliment a patient's regular breathing. Positive airway positive airway pressure therapy may be used to maintain an open airway in a patient so that oxygen and carbon dioxide may be exchanged more easily, requiring little and/or no effort from the patient. By way of non-limiting example, control component 40 may control pressure generator 14 such that the pressure therapy provided to subject 12 via the flow of gas comprises continuous positive airway pressure support (CPAP), bi-level positive airway pressure support (BPAP), proportional positive airway pressure support (PPAP), forced oscillation technique, and/or other types of positive airway pressure therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), control component 40 may control pressure generator 14 to apply variable pressure therapy in which the amount of pressure delivered to subject 12 during inhalation and/or during exhalation is determined and delivered on a breath by breath basis. In some embodiments, control component 40 may be configured to control pressure generator 14 to temporarily drop the supplied pressure during exhalation (C-Flex) to reduce exhalation effort required by subject 12.

In some embodiments, control component 40 is configured to control pressure generator 14 to deliver staged pressure therapy. In staged positive airway pressure therapy, the pressure delivered by pressure generator 14 gradually increases over time. In some embodiments, control component 40 may control pressure generator 14 to switch therapy modes based on information related to the respiration of subject 12 and/or other information. For example, control component 40 may control pressure generator 14 to change from BPAP to CPAP after a certain number of breaths by subject 12.

In some embodiments, control component 40 is configured to determine one or more parameters within system 10, and control the pressurized flow of breathable gas based on the parameters. The one or more parameters within system 10 may comprise gas parameters related to the pressurized flow of breathable gas (e.g., as described above), respiration parameters related to the breathing of subject 12 (e.g., as described above), and/or other parameters. Control component 40 may be configured to determine the one or more parameters based on the output signals of sensors 18, for example. The information determined by control component 40 may be used for controlling pressure generator 14, stored in electronic storage 52, and/or used for other uses.

In some embodiments, control component 40 is configured to determine the respiratory phase (e.g., inhalation, exhalation) during breathing of subject 12. The respiratory phase determinations made by control component 40 are based on the output signals from sensors 18, the determined parameters, and/or other information. These determinations may be used by control component 40 to control pressure generator 14 to control the pressurized flow of breathable gas delivered to subject 12, control the stimulation delivered to subject 12 (as described below), may be stored in electronic storage 52, and/or used for other uses. In some embodiments, control component 40 is configured to determine the respiratory phase (e.g., inhalation, exhalation) based on changes in pressure, flow rate, and/or other determined parameters.

Sleep stage component 42 is configured to determine the sleep stages of subject 12. The sleep stages are determined based on the information in the output signals, parameters determined by control component 40, and/or other information. In some embodiments, the sleep stages indicate presence of sleep, depth of sleep, and/or other characteristics of subject 12 during the sleep session. In some embodiments, sleep stage component 42 is configured such that determining the sleep stages of subject 12 includes determining and/or receiving (e.g., from control component 40) one or more respiratory activity parameters, brain activity parameters, and/or other parameters for subject 12. In some embodiments, sleep stage component 42 is configured to determine the sleep stages, the one or more respiratory and/or brain activity parameters described above, and/or other information at predetermined times (e.g., intervals), substantially continuously, and/or at other times. In some embodiments, sleep stage component 42 is configured to determine sleep stages (e.g., wake, REM, N1, N2, N3) or some combination of sleep stages, such as wake, REM, light sleep (N1/N2), and deep sleep (N3), while subject 12 is sleeping and/or before or after a sleep session.

In some embodiments, the information in the output signals and/or the parameters that are used to determine the sleep stages of subject 12 comprise output signals and/or parameters related to respiration of subject 12. For example, the information in the output signals and/or the parameters that are used to determine the sleep stages of subject 12 may include a pressure and/or a flow rate of the pressurized flow of breathable gas inhaled and exhaled by subject 12 over time, and/or other information. In other words, sleep stage component 42 is configured to automatically determine sleep stages of subject 12 using signal modalities (e.g., information in the output signals from sensor(s) 18 available from the PAP device functionality of system 10. In some embodiments, sleep stage component 42 may use airflow (and/or pressure, etc.) information measured during PAP therapy to detect individual patient breaths (e.g., comprising an inhalation and exhalation). For example, sleep stage component 42 may characterize and/or otherwise identify one or more features of an air flow, pressure, and/or other output signals for individual breaths.

Examples of features may include: tidal volume, minute ventilation, duration of inhalation, duration of exhalation, peak inspiratory flow, peak expiratory flow, slew rates, and other features. Sleep stage component 42 may determine one or more statistics (e.g., averages, maximum, minimums, standard deviations, statistics indicative of changes in data, etc.) based on the identified features. The statistical determinations may be made for one or more windows of the output signals of different lengths of time. The sleep stage determinations may be made based on these statistical determinations and/or other information. In some embodiments, sleep stage component 42 may use a pre-trained neural network model to automatically classify sleep stages based on the analysis of the feature statistics.

In some embodiments, the information in the output signals and/or the parameters that are used to determine the sleep stages of subject 12 comprise output signals and/or parameters related to brain activity in subject 12. In some embodiments, the one or more brain activity parameters are determined by sleep stage component 42 based on the respiratory activity parameters, and/or other information. In some embodiments, determining one or more brain activity parameters may include generating and/or monitoring an EEG during a sleep session of subject 12. The EEG may be displayed, for example, by user interface 50. In some embodiments, sleep stage component 42 is configured such that the one or more brain activity parameters are and/or are related to a frequency, amplitude, phase, presence of specific sleep patterns such as spindles, K-complexes, or sleep slow waves, alpha waves, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate sleep stages that correspond to the REM and/or NREM sleep stages described above.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 4 Hz), also known as sleep slow waves, with peak-to-peak amplitudes greater than about 75 uV for sleep stage N3; presence of light sleep and/or arousals, and/or other characteristics. In some embodiments, light sleep may be characterized by the fact that the alpha activity (e.g., EEG power in the 8-12 Hz band) is no longer present and slow waves are not present.

In some embodiments, slow wave activity is a continuous value (e.g., EEG power in the 0.4 to 4 Hz band), which is positive.

System 10 may be configured to detect its absence by comparing the slow wave activity in subject 12 to a threshold. In some embodiments, an absence of slow waves is indicative of light sleep. In addition, spindle activity (EEG power in the 11 to 16 Hz band) may be high. Deep sleep may be characterized by the fact that delta activity (e.g., EEG power in the 0.5 to 4 Hz band) is dominant. In some embodiments, EEG power in the delta band and slow wave activity are the same with respect to sleep EEG. In some embodiments, sleep stage component 42 is configured to determine a change in an EEG delta power level caused by stimulation, a quantity of micro arousals in subject 12, other EEG power levels, and/or other parameters. In some embodiments, sleep stage component 42 is configured to determine a level of slow wave activity in subject 12, detect slow wave events, detect N1, N2, and/or N3 sleep, and/or determine other information. In some embodiments, sleep stage component 42 is configured to determine a type of (e.g., NREM) sleep by, for example, determining EEG power in the 0.5 to 4 Hz frequency band, which indicates slow wave activity, and quantifying a density of slow waves in the EEG signal. In some embodiments, slow waves may not be present throughout the whole N3 period, for example, but it may be significantly more likely that such slow waves are present during N3. Slow waves may also be present (although to a lesser extent) during N2, for example.

Stimulation component 44 is configured to, responsive to the sleep stages indicating subject 12 is in deep sleep, cause pressure generator 14 to adjust the pressurized flow of breathable gas to deliver a stimulus to subject 12. The stimulus is configured to enhance the deep sleep in subject 12. In some embodiments, the stimulus is configured to facilitate a transition to a deeper stage of sleep, a lighter stage of sleep, maintain sleep in a specific stage, enhance the restorative effects of sleep, and/or for other purposes. In some embodiments, stimulation component 44 may be configured such that facilitating a transition between lighter sleep stages and deeper sleep stages includes increasing sleep slow waves. In some embodiments, the stimulus provided to subject 12 may be repeated one or more times. The stimulus may be repeated during an individual episode of deep sleep, across multiple episodes of deep sleep, throughout a sleep session, and/or at other times.

In some embodiments, causing pressure generator 14 to adjust the pressurized flow of breathable gas to deliver the stimulus to subject 12 comprises causing motor oscillations in pressure generator 14, which in turn, cause oscillations in the pressure and/or flow rate of the pressurized flow of breathable gas delivered to subject 12. The oscillations may include pressure pulses, gas boluses, perturbations in the flow rate, cessation of flow, and/or other oscillations. In some embodiments, stimulation component 44 is configured to cause oscillations in the pressure and/or flow rate in other ways (e.g., via one or more valves included in system 10, etc.). In some embodiments, stimulation component 44 is configured to cause pressure generator 14 to perform the motor oscillations, for example. In some embodiments, causing the motor oscillations in the pressure generator comprises determining a timing, a frequency, and/or an intensity of the motor oscillations based on the output signals to enhance deep sleep in the subject. By way of a non-limiting example, stimulation component 44 may cause a 50% duty cycle pulse 1 cmH2O peak to peak at a frequency of 1 hertz.

In some embodiments, as described above, system 10 comprises an external sensory stimulation device 19 operatively coupled to, and controlled by, stimulation component 44. In some embodiments, external sensory stimulation device 19 comprises one or more external sensory stimulation devices 19 of one or more different types (e.g., tone generators, light generators, electromagnetic stimulators, etc.). In some embodiments, stimulation component 44 is configured to cause external sensory stimulation device 19 to deliver external sensory stimulation to subject 12. The external sensory stimulation may be in addition to or instead of the stimulus provided by the pressurized flow of breathable gas. In some embodiments, the external sensory stimulation comprises auditory stimulation, light stimulation, electromagnetic stimulation, and/or other stimulation (e.g., as described above related to external sensory stimulation device 19).

For example, as described above, stimulation component 44 may control external sensory stimulation device 19 to provide acoustic tones to subject 12 to enhance the restorative effects of sleep in subject 12. The acoustic tones may have a frequency, rate, timing, intensity (volume and/or duration) and/or other characteristics determined by external sensory stimulation device 19 and/or other components of system 10. The acoustic tones may include one or more series of tones separated from each other by an inter-tone interval. The volume of individual tones may be modulated by sleep depth. This example is not intended to be limiting. Similar examples with light stimulation, electromagnetic stimulation, vibratory stimulation, olfactory stimulation, and/or other types of stimulation are contemplated.

In some embodiments, the stimulus provided by the pressurized flow of breathable gas and/or the auditory (or other) stimulation is delivered to subject 12 through subject interface 16. For example, the oscillations in the pressurized flow of breathable gas caused by pressure generator 14 may travel through conduit 30 and interface appliance 32 to reach subject 12. As another example, a tone generator, speaker, scent generator, or other external sensory stimulation device 19 may be coupled to and/or otherwise in communication with conduit 30 and/or interface appliance 32 such that sounds, smells, etc. travel down conduit 30 and interface appliance 32 to reach subject 12. In some embodiments, external sensory stimulation device 19 may be coupled to one more other locations in system 10. For example, a speaker and/or a lighting device may be coupled to pressure generator 14, a surface of conduit 30, a surface of interface appliance 32, and/or other components of system 10. In some embodiments, electrodes, for example, may be coupled to a portion of interface appliance 32 that contacts the head or face of subject 12. In some embodiments, the sensory stimulation is delivered through the atmosphere surrounding subject 12 (e.g., a speaker may project sound through the air, a lighting device may project light, electromagnetic stimulation may be delivered through the skin, etc.).

Figure 2:
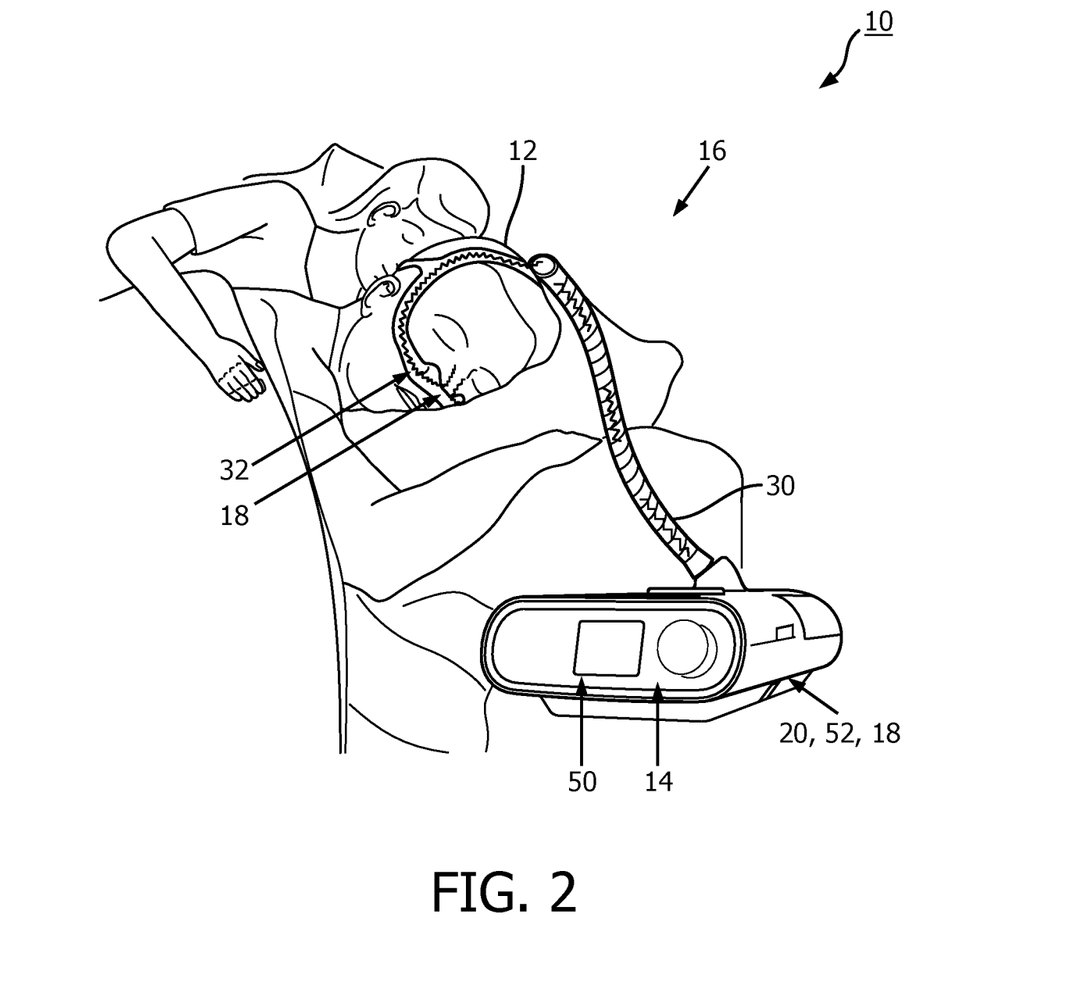
FIG. 2 illustrates a possible embodiment of the system.

By way of a non-limiting example, one possible embodiment of system 10 is illustrated in FIG. 2. FIG. 2 illustrates examples of subject 12, pressure generator 14, subject interface 16 including conduit 30 and interface appliance 32, and user interface 50. In the embodiment shown in FIG. 2, pressure generator 14 may include processor 20, electronic storage 52, one or more sensors 18 (another possible location for sensors 18 is also illustrated), and other components. Pressure generator 14 (controlled by control component 40 (FIG. 1) of processor 20) may provide positive airway pressure (PAP) therapy for subject 12 during a sleep session.

The pressurized flow of breathable gas may be delivered to subject 12 by subject interface 16 (via conduit 30 and interface appliance 32 as shown in FIG. 2) and controlled based on output signals from sensors 18. Sleep stage component 42 (FIG. 1) of processor 20 may receive and/or otherwise collect the information in the output signals from sensors 18 and determine the sleep stage of subject 12 based on the information in the output signals. Responsive to determining subject 12 is in deep (or delta) sleep, stimulation component 44 (FIG. 1) of processor 20 is configured to cause pressure generator 14 to generate a deep (or delta) sleep enhancing stimulus.

In some embodiments, the stimulus is then delivered to subject 12 via subject interface 16 to enhance the deep (or delta) sleep slow waves in subject 12. In some embodiments, the pressurized flow of breathable gas is adjusted to deliver a stimulus to subject 12. In some embodiments, adjusting the pressurized flow of breathable gas to deliver the stimulus to subject 12 comprises causing motor oscillations in pressure generator 14, which in turn, cause oscillations in the pressure and/or flow rate of the pressurized flow of breathable gas delivered to subject 12. In some embodiments, stimulation component 44 is configured to cause pressure generator 14 to perform the motor oscillations, for example. In some embodiments, causing the motor oscillations in the pressure generator comprises determining a timing, a frequency, and/or an intensity of the motor oscillations based on the output signals to enhance deep sleep in subject 12.

In some embodiments, system 10 comprises an external sensory stimulation device (not shown in FIG. 2) operatively coupled to, and controlled by, processor 20. In some embodiments, the external sensory stimulation device, delivers (e.g., controlled by stimulation component 44 (FIG. 1)) external sensory stimulation to subject 12 in addition to or instead of the stimulus provided by the pressurized flow of breathable gas. In some embodiments, the external sensory stimulation device is and/or includes a speaker, a lighting device, electrodes, and/or other devices. In some embodiments, the external sensory stimulation device may be coupled to one more other components of system 10. For example, a speaker and/or a lighting device may be coupled to pressure generator 14, conduit 30, interface appliance 32, and/or other components of system 10. In some embodiments, electrodes, for example, may be coupled to a portion of interface appliance 32 that contacts the head or face of subject 12. In some embodiments, the sensory stimulation is delivered through the atmosphere surrounding subject 12 (e.g., a speaker may project sound through the air, a lighting device may project light, etc.). In some embodiments, the sensory stimulation may be delivered through conduit 30 and/or interface appliance 32 (e.g., pressure and/or flow fluctuations, tones may be projected through conduit 30, a tapping sensation may be provided to one or more parts of the body, etc.).

Figure 3:
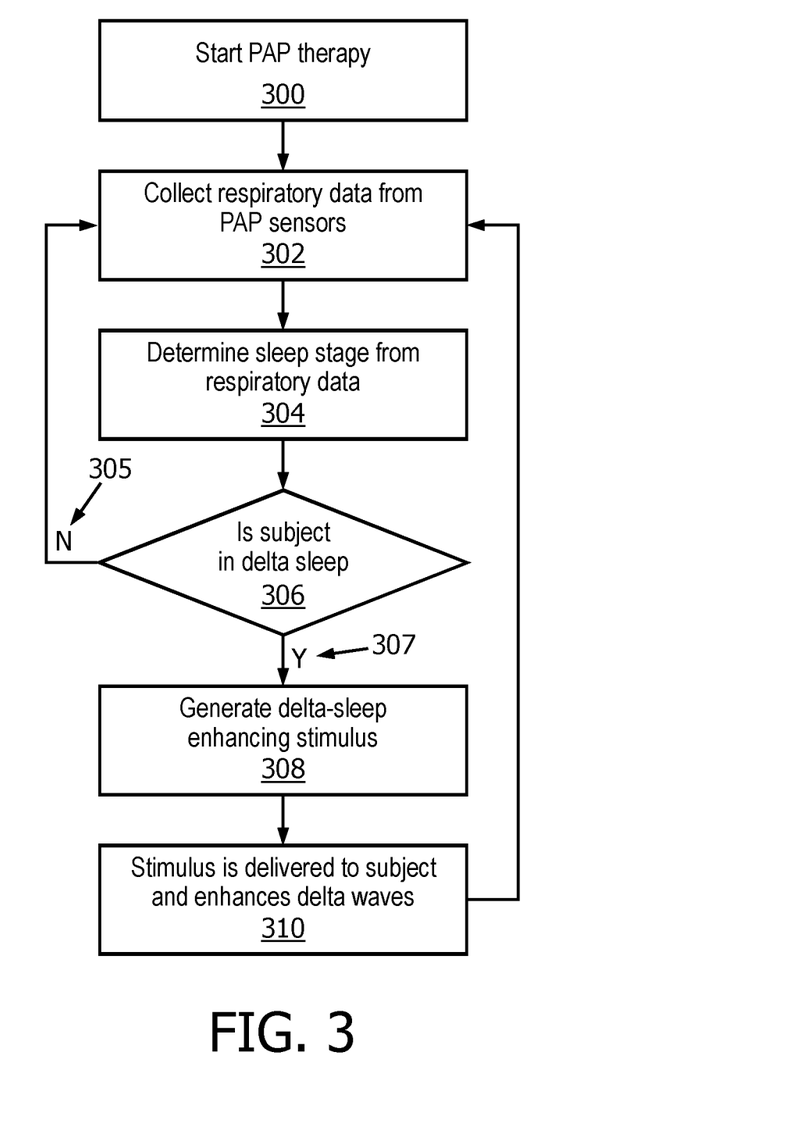
FIG. 3 illustrates operations performed by the system.

FIG. 3 illustrates example operations 300-310 performed by system 10 (FIG. 1). As shown in FIG. 3, operations 300-310 begin with starting positive airway pressure (PAP) therapy 300 for a subject (e.g., subject 12 shown in FIG. 1). For example, control component 40 (FIG. 1) may cause pressure generator 14 (FIG. 1) to generate a pressurized flow of breathable gas according to a PAP therapy regime. The pressurized flow of breathable gas may be delivered to the subject by subject interface 16 (FIG. 1) and controlled based on output signals from sensors 18 (FIG. 1). At operation 302, sleep stage component 42 (FIG. 1) may receive and/or otherwise collect the information in the output signals from sensors 18 (e.g., collect respiratory data from PAP sensors)

and determine 304 the sleep stage of the subject based on the information in the output signals (e.g., the respiratory data). Responsive to determining the subject is in deep (or delta) sleep ("Yes" 307), stimulation component 44 (FIG. 1) is configured to cause pressure generator 14 to generate a deep (or delta) sleep enhancing stimulus 308. The stimulus is then delivered to the subject via subject interface 16 to enhance the deep (or delta) sleep slow waves in the subject. Responsive to determining the subject is not in deep (or delta) sleep, the system continues to collect respiratory data from sensors 18 (operation 302) and determine sleep stages of the subject based on the respiratory data.

Returning to FIG. 1, user interface 50 is configured to provide an interface between system 10 and user 12, and/or other users through which user 12 and/or other users may provide information to and receive information from system 10. This enables data, cues, results, and/or instructions and any other communicable items, collectively referred to as "information," to be communicated between a user (e.g., user 12) and one or more of pressure generator 14, sensor 18, external sensory stimulation devices 19, processor 20, electronic storage 52, external resources 54, and/or other components of system 10. For example, a hypnogram, sleep stage, and/or other information may be displayed for subject 12 and/or other users via user interface 50. User interface 50 may be included in and/or coupled to pressure generator 14, sensors 18, external sensory stimulation devices 19, processors 20, electronic storage 52, external resources 54, and/or other components of system 10. As another example, user interface 50 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users.

Examples of interface devices suitable for inclusion in user interface 50 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 50 comprises a plurality of separate interfaces. In some embodiments, user interface 50 comprises at least one interface that is provided integrally with pressure generator 14, processor 20, and/or other components of system 10. In some embodiments, user interface 50 is configured to communicate wirelessly with processor 20 and/or other components of system 10.

It is to be understood that other communication techniques, either hard-wired or wireless, are also contemplated by the present disclosure as user interface 50. For example, the present disclosure contemplates that user interface 50 may be integrated with a removable storage interface provided by electronic storage 52. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 50 comprise, but are not limited to, an RS-232 port, RF link, an IR link, modem (telephone, cable or other). In short, any technique for communicating information with system 10 is contemplated by the present disclosure as user interface 50.

Electronic storage 52 comprises electronic storage media that electronically stores information. The electronic storage media of electronic storage 52 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 52 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 52 may store software algorithms, information determined by processor 20, information received via user interface 50 and/or external computing systems (e.g., external resources 54), and/or other information that enables system 10 to function as described herein. Electronic storage 52 may be (in whole or in part) a separate component within system 10, or electronic storage 52 may be provided (in whole or in part) integrally with one or more other components of system 10 (e.g., processor 20).

External resources 54 include sources of information (e.g., databases, websites, etc.), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 54 may be provided by resources included in system 10. External resources 54 may be configured to communicate with processor 20, user interface 50, sensor 18, electronic storage 52, external sensory stimulation device 19, and/or other components of system 10 via wired and/or wireless connections, via a network (e.g., a local area network and/or the internet), via cellular technology, via Wi-Fi technology, and/or via other resources.

Figure 4:
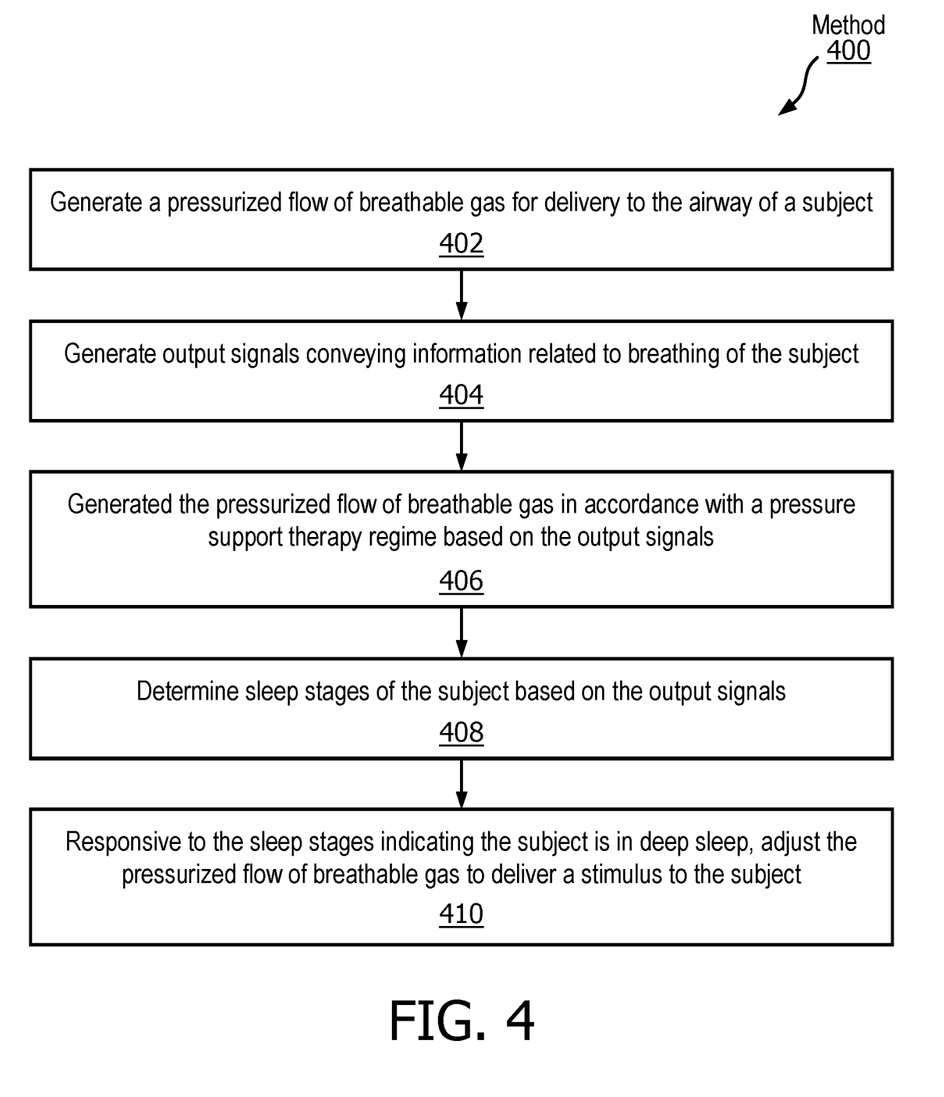
FIG. 4 illustrates a method for enhancing deep sleep in a subject during positive airway pressure therapy.

FIG. 4 illustrates method 400 for delivering sensory stimulation to a subject (e.g., subject 12) during deep sleep in a sleep session with a delivery system. The system comprises a pressure generator, one or more sensors, one or more hardware processors configured by machine-readable instructions, and/or other components. The one or more hardware processors are configured to execute computer program components. The computer program components comprise a control component, a sleep stage component, a stimulation component, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium.

The one or more processing devices may include one or more devices configured through hardware, firmware, and/or software to be specifically designed for execution of one or more of the operations of method 400.

At an operation 402, a pressurized flow of breathable gas is generated for delivery to the airway of a subject. In some embodiments, operation 402 is performed by a pressure generator the same as or similar to pressure generator 14 (shown in FIG. 1 and described herein).

At an operation 404, output signals conveying information related to breathing of the subject are generated. In some embodiments, the information in the output signals that is used to determine the sleep stages of the subject comprises one or both of a pressure and a flow rate of the pressurized flow of breathable gas inhaled and exhaled by the subject over time, and/or other information. In some embodiments, operation 404 is performed by one or more sensors the same as or similar to sensors 18 (shown in FIG. 1 and described herein). In some embodiments, the one or more sensors comprise a flow rate sensor configured to generate output signals conveying information related to a flow rate of the pressurized flow of breathable gas, and a pressure sensor conveying information related a pressure of breathable gas, and/or other sensors.

At an operation 406, the pressurized flow of breathable gas is generated in accordance with a positive airway pressure therapy regime. The pressurized flow of breathable gas is generated based on the output signals and/or other information. In some embodiments, operation 406 is performed by system components the same as or similar to pressure generator 14, sensors 18, and/or control component 40 (shown in FIG. 1 and described herein).

At an operation 408, sleep stages of the subject are determined. The sleep stages are determined based on the output signals and/or other information. In some embodiments, operation 408 is performed by a processor component the same as or similar to sleep stage component 42 (shown in FIG. 1 and described herein).

At an operation 410, responsive to the sleep stages indicating the subject is in deep sleep, the pressurized flow of breathable gas is adjusted to deliver a stimulus to the subject. In some embodiments, adjusting the pressurized flow of breathable gas to deliver the stimulus to the subject comprises causing motor oscillations in the pressure generator which, in turn, cause oscillations in the pressure and/or flow rate of the pressurized flow of breathable gas delivered to the subject. In some embodiments, operation 410 is performed by a processor component the same as or similar to stimulation component 44 (shown in FIG. 1 and described herein).

In some embodiments, stimulation component 44 is configured to cause pressure generator 14 to perform the motor oscillations, for example. In some embodiments, causing the motor oscillations in the pressure generator comprises determining a timing, a frequency, and/or an intensity of the motor oscillations based on the output signals to enhance deep sleep in the subject. In some embodiments, the system further comprises an external sensory stimulation device operatively coupled to, and controlled by, the one or more hardware processors. In some embodiments, the method further comprises delivering, with the external sensory stimulation device, external sensory stimulation to the subject in addition to or instead of the stimulus provided by the pressurized flow of breathable gas. In some embodiments, the external sensory stimulation comprises auditory stimulation or electromagnetic stimulation. In some embodiments, the system further comprises a subject interface configured to conduct the pressurized flow of breathable gas from the pressure generator to the airway of the subject. In some embodiments, the stimulus provided by the pressurized flow of breathable gas and/or the auditory stimulation is delivered to the subject through the subject interface.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to enhance deep sleep in a subject during positive airway pressure therapy, the system comprising:

a pressure generator configured to generate a pressurized flow of breathable gas for delivery to an airway of the subject;

one or more sensors configured to generate output signals conveying information related to breathing of the subject; and one or more hardware processors operatively coupled to the pressure generator and the one or more sensors, the one or more hardware processors configured by machine-readable instructions to:

cause the pressure generator to generate the pressurized flow of breathable gas in accordance with a positive airway pressure therapy regime based on the information in the output signals;

determine sleep stages of the subject based on the information in the output signals; and responsive to the sleep stages indicating the subject is in deep sleep, cause the pressure generator to adjust the pressurized flow of breathable gas to deliver a stimulus to the subject, the stimulus configured to enhance deep sleep in the subject, the stimulus comprising pressure pulses, gas boluses, pertubations in a flow rate, and/or cessation of flow, of the pressurized flow of breathable gas, and the stimulus being repeated during an individual episode of deep sleep, and across multiple episodes of deep sleep to enhance delta waves in the subject.

2. The system of claim 1, wherein the one or more hardware processors are configured such that causing the pressure generator to adjust the pressurized flow of breathable gas to deliver the stimulus to the subject comprises causing motor oscillations in the pressure generator which, in turn, cause the pressure pulses, gas boluses, perturbations in the flow rate, and/or cessation of flow of the pressurized flow of breathable gas delivered to the subject.

3. The system of claim 2, wherein the one or more hardware processors are configured such that causing the motor oscillations in the pressure generator comprises determining a timing, a frequency, and/or an intensity of the motor oscillations based on the output signals to cause a stimulus comprising a 50% duty cycle pulse 1 cmH2O peak to peak at a frequency of 1 hertz to enhance deep sleep in the subject.

4. The system of claim 1, wherein the one or more sensors and the one or more hardware processors are configured such that the information in the output signals used to determine the sleep stages of the subject comprises one or both of a pressure and a flow rate of the pressurized flow of breathable gas inhaled and exhaled by the subject over time.

5. The system of claim 1, wherein the one or more sensors comprise a flow rate sensor configured to generate output signals conveying information related to a flow rate of the pressurized flow of breathable gas, and a pressure sensor conveying information related a pressure of breathable gas.

6. The system of claim 1, further comprising an external sensory stimulation device operatively coupled to, and controlled by, the one or more hardware processors and configured to deliver external sensory stimulation to the subject in addition to or instead of the stimulus provided by the pressurized flow of breathable gas, the external sensory stimulation comprising electromagnetic stimulation.

7. A method for enhancing deep sleep in a subject during positive airway pressure therapy with an enhancement system, the system comprising a pressure generator, one or more sensors, and one or more hardware processors configured by machine-readable instructions, the method comprising:
  generating, with the pressure generator, a pressurized flow of breathable gas for delivery to an airway of the subject;
  generating, with the one or more sensors, output signals conveying information related to breathing of the subject;
  causing, with the one or more hardware processors, the pressure generator to generate the pressurized flow of breathable gas in accordance with a positive airway pressure therapy regime based on the information in the output signals;
  determining, with the one or more hardware processors, sleep stages of the subject based on the information in the output signals; and
  responsive to the sleep stages indicating the subject is in deep sleep, causing, with the one or more hardware processors, the pressure generator to adjust the pressurized flow of breathable gas to deliver a stimulus to the subject, the stimulus configured to enhance deep sleep in the subject, the stimulus comprising pressure pulses, gas boluses, pertubations in a flow rate, and/or cessation of flow, of the pressurized flow of breathable gas, and the stimulus being repeated during an individual episode of deep sleep, and across multiple episodes of deep sleep to enhance delta waves in the subject.

8. The method of claim 7, wherein the information in the output signals used to determine the sleep stages of the subject comprises one or both of a pressure and a flow rate of the pressurized flow of breathable gas inhaled and exhaled by the subject over time.

9. The method of claim 8, wherein the system further comprises an external sensory stimulation device operatively coupled to, and controlled by, the one or more hardware processors, the method further comprising delivering, with the external sensory stimulation device, external sensory stimulation to the subject in addition to or instead of the stimulus provided by the pressurized flow of breathable gas, the external sensory stimulation comprising electromagnetic stimulation.

10. The method of claim 7, wherein the one or more sensors comprise a flow rate sensor configured to generate output signals conveying information related to a flow rate of the pressurized flow of breathable gas, and a pressure sensor conveying information related a pressure of breathable gas.

11. The method of claim 7, wherein causing the pressure generator to adjust the pressurized flow of breathable gas to deliver the stimulus to the subject comprises causing motor oscillations in the pressure generator which, in turn, cause the pressure pulses, gas boluses, perturbations in the flow rate, and/or cessation of flow of the pressurized flow of breathable gas delivered to the subject, wherein causing the motor oscillations in the pressure generator comprises determining a timing, a frequency, and/or an intensity of the motor oscillations based on the output signals to cause a stimulus comprising a 50% duty cycle pulse 1 cmH2O peak to peak at a frequency of 1 hertz to enhance deep sleep in the subject.

12. A system for enhancing deep sleep in a subject during positive airway pressure therapy, the system comprising:
  means for generating a pressurized flow of breathable gas for delivery to an airway of the subject;
  means for generating output signals conveying information related to breathing of the subject;
  means for causing the means for generating the pressurized flow of breathable gas to generate the pressurized flow of breathable gas in accordance with a positive airway pressure therapy regime based on the information in the output signals;
  means for determining sleep stages of the subject based on the information in the output signals; and
  means for, responsive to the sleep stages indicating the subject is in deep sleep, causing the means for generating the pressurized flow of breathable gas to adjust the pressurized flow of breathable gas to deliver a stimulus to the subject, the stimulus configured to enhance deep sleep in the subject, the stimulus comprising pressure pulses, gas boluses, pertubations in a flow rate, and/or cessation of flow, of the pressurized flow of breathable gas, and the stimulus being repeated during an individual episode of deep sleep, and across multiple episodes of deep sleep to enhance delta waves in the subject.

13. The system of claim 12, wherein the information in the output signals used to determine the sleep stages of the subject comprises one or both of a pressure and a flow rate of the pressurized flow of breathable gas inhaled and exhaled by the subject over time.

14. The system of claim 12, wherein the means for generating output signals comprise a flow rate sensor configured to generate output signals conveying information related to a flow rate of the pressurized flow of breathable gas, and a pressure sensor conveying information related a pressure of breathable gas.

15. The system of claim 12, wherein causing the means for generating the pressurized flow of breathable gas to adjust the pressurized flow of breathable gas to deliver the stimulus to the subject comprises causing motor oscillations in the means for generating the pressurized flow of breathable gas which, in turn, cause the pressure pulses, gas boluses, perturbations in the flow rate, and/or cessation of flow of the pressurized flow of breathable gas delivered to the subject, wherein causing the motor oscillations in the pressure generator comprises determining a timing, a frequency, and/or an intensity of the motor oscillations based on the output signals to cause a stimulus comprising a 50% duty cycle pulse 1 cmH2O peak to peak at a frequency of 1 hertz to enhance deep sleep in the subject.

\* \* \* \* \*